United States Patent
Garnier et al.

(10) Patent No.: US 7,070,770 B1
(45) Date of Patent: Jul. 4, 2006

(54) COMPOSITIONS FOR THE PERMANENT DEFORMATION OF THE HAIR COMPRISING AT LEAST ONE FORMAMIDINESULPHINIC ACID DERIVATIVE

(76) Inventors: Nathalie Garnier, 2345 Promenade Pl., Scotch Plains, NJ (US) 07076; Gérard Malle, 18 Grande Rue, 77580 Villiers sur Morin (FR); Henri Samain, 14, Rue du Coteau, 91570 Bievres (FR)

( * ) Notice: Subject to any disclaimer, the term of this patent is extended or adjusted under 35 U.S.C. 154(b) by 0 days.

(21) Appl. No.: 09/714,663

(22) Filed: Nov. 17, 2000

(51) Int. Cl.
  *A61K 8/00* (2006.01)
  *A61K 8/58* (2006.01)
  *A61K 8/49* (2006.01)
  *A61K 8/19* (2006.01)

(52) U.S. Cl. ............ 424/70.2; 424/70.11; 424/70.2; 424/70.4; 424/70.6; 424/70.8; 424/70.9; 424/70.22; 424/70.27; 424/70.28; 424/70.31; 424/70.19; 424/70.21

(58) Field of Classification Search ........... 424/70.1, 424/70.2, 70.11, 70.9; 546/152, 176
See application file for complete search history.

(56) References Cited

U.S. PATENT DOCUMENTS 3,051,626 A * 8/1962 Rao .................. 167/78
3,715,429 A   2/1973 Amon ............... 424/71
4,314,810 A * 2/1982 Fourcadier et al. ....... 8/410

FOREIGN PATENT DOCUMENTS

| DE | 1035322 | | 7/1958 |
|---|---|---|---|
| DE | 1198491 | | 8/1965 |
| DE | 2111697 | | 9/1972 |
| GB | 1202601 | * | 8/1970 |
| GB | 1334636 | | 10/1973 |

OTHER PUBLICATIONS

Yarovenko et al. (DN 73:34993, CAPLUS, abstract of Zh. Org. Khim. (1970), 6(5), 947-9).*
Shobanov et al. (DN 70:87599, CAPLUS, abstract of SU 229521).*
Yarovenko et al., Database CA Accession No. 73:34993 XP-002222110 abstract.

* cited by examiner

*Primary Examiner*—Sabiha Qazi
(74) *Attorney, Agent, or Firm*—Finnegan, Henderson, Farabow, Garrett & Dunner, LLP

(57) ABSTRACT

The invention relates to a reducing composition for the permanent deformation of the hair comprising an N-substituted formamidinesulphinic acid derivative as reducing agent and to a process for the permanent deformation of the hair employing this reducing composition.

83 Claims, No Drawings

COMPOSITIONS FOR THE PERMANENT DEFORMATION OF THE HAIR COMPRISING AT LEAST ONE FORMAMIDINESULPHINIC ACID DERIVATIVE

A subject-matter of the invention is a composition for the permanent deformation of the hair comprising at least one formamidinesulphinic acid derivative. The invention is also targeted at a process for the permanent deformation of the hair employing this composition.

The technique for bringing about the permanent deformation of the hair consists, in a first step, in opening the disulphide bonds of the keratin (cystine) using a composition comprising a reducing agent (reduction stage) and then, preferably after having rinsed the hair, in reconstituting, in a second step, the said disulphide bonds by applying an oxidizing composition to the hair under tension (oxidation stage, also known as setting stage), so as to give the hair the desired shape. This technique makes it possible without distinction to either wave the hair or to straighten it.

The compositions for carrying out the first stage of a perming operation are generally provided in the form of lotions, creams, gels or powders to be diluted in a liquid vehicle and comprise a reducing agent, preferably a thiol. Among the latter, those commonly used are cysteine and thioglycolic acid and its esters, in particular glyceryl monothioglycolate. Thioglycolic acid is particularly effective in reducing the disulphide bonds of keratin and can be regarded, at alkaline pH, in particular in the form of ammonium thioglycolate, as the reference compound in permanent waving. However, it exhibits a disadvantage of giving off an unpleasant smell. A fragrance which allows smells to be masked is generally used for the purpose of overcoming this disadvantage.

Cysteine has a much fainter smell than that of thioglycolic acid but the degree of curling obtained is much less and far from being satisfactory. Furthermore, cysteine requires the use of a highly alkaline pH.

Glyceryl monothioglycolate is also highly malodorous. In contrast, it is used at a pH close to neutrality but its performance is appreciably inferior to that of thioglycolic acid.

Various studies have been carried out for the purpose of overcoming the disadvantages of these reducing agents and, to this end, the use of novel reducing compounds has been proposed. Thus, U.S. patent application No. 3,715,429 has disclosed a composition for the deformation of the hair comprising thiourea dioxide in combination with an activating agent.

Nevertheless, the reducing compositions for permanent waves known to date are still not entirely satisfactory, given that damage to the hair fibre is excessively great.

The problem posed by the invention is to provide a reducing composition for the permanent deformation of the hair which is more effective than those which already exist, in particular in terms of degree, of liveliness or of quality of curling, while reducing the damage to the hair.

To solve this problem, the invention provides a reducing composition for the permanent deformation of the hair, characterized in that it comprises, as reducing agent, an N-substituted formamidinesulphinic acid derivative of following general formula (I):

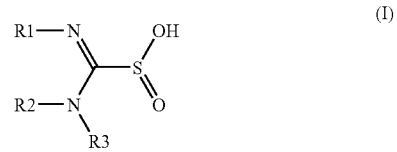

in which:

(a) R1, R2 and R3, which are identical or different, represent a hydrogen atom, an amino, C1 to C8 amino-alkyl, imino, C1 to C8 aminoalkyl or guanidino group, a C1 to C8 linear or branched alkyl, C2 to C8 alkenyl or C7 to C20 aralkyl group, or an aromatic or nonaromatic C3 to C20 ring optionally comprising one or more heteroatom(s) chosen from halogens, nitrogen, oxygen or sulphur; it being possible for all these substituents optionally to carry one or more hydroxyl, carboxyl, amino, amido, halogen, C1–C8 alkyl or C1–C8 alkoxy radicals, and (b) at least one of the R1, R2 or R3 groups is an amino or C1 to C8 aminoalkyl group or is chosen from the alkyls, alkenyls, aralkyls, aryls or rings listed above in (a), these groups being, in addition, either directly substituted by at least one sulphonyl, sulphonate, phosphonyl, phosphate, amino or C1 to C8 alkoxy radical or substituted by another C1 to C8 alkyl, C2 to C8 alkenyl or C7 to C20 aralkyl group, themselves substituted by a sulphonic acid, sulphonate, phosphoric acid, phosphate, amino or C1 to C8 alkoxy radical;

and the inorganic or organic salts of the said compounds of formula (I).

The invention also relates to the use of a compound of formula (I) as reducing agent, in particular in a reducing composition intended for the permanent deformation or the straightening of the hair.

Yet another subject-matter of the invention relates to a process for the permanent deformation of the hair employing a reducing composition comprising at least one compound of formula (I).

The R1, R2 and R3 groups chosen in order to obtain a compound of formula (I) as defined above are preferably selected from:

the hydrogen atom, linear or branched C1–C6 alkyls optionally substituted by at least one hydroxyl, carboxyl, amino, sulphonyl or phosphonyl radical, phenyls optionally substituted by at least one halogen atom or by a C1–C4 alkyl or C1–C4 alkoxy radical or alternatively hydroxyl, heterocycles, such as pyridine, dihydropyridine, tetrahydropyridine or quinoline, and the guanidino radical.

The compounds of formula (I) are generally prepared according to the procedures disclosed in the following references:

E. Ya. Yarovenko et al., Zh. Org. Khim. (1970), 6 (5), 947–9;

M. F. Kondrachova et al., Metody Poluch. Khim. Reaktivov Prep. (1969), No. 20, 56–7;

D. De Filippo et al., J. Chem. Soc. Perkin Trans. II (1972), (11), 1500–2;

J. J. Havel et al., Synth. Commun. (1974), 4 (6), 389–93; and

Patent Applications SU 229521 and EP-A1 488749.

Mention may in particular be made, among the preferred compounds of general formula (I), of:
imino(methylamino)methanesulphinic acid
imino(propylamino)methanesulphinic acid
(dimethylamino)iminomethanesulphinic acid
(diethylamino)iminomethanesulphinic acid
(ethylamino)(ethylimino)methanesulphinic acid
(methylamino)(methylimino)methanesulphinic acid
(ethylamino)(ethylimino)methanesulphinic acid
(butylamino)(butylimino)methanesulphinic acid
(phenylamino)(phenylimino)methanesulphinic acid
(phenylmethylamino)(phenylmethylimino)-methanesulphinic acid
(carboxymethylamino)iminomethanesulphinic acid
(2-carboxyethylamino) iminomethanesulphinic acid
(3-carboxypropylamino)iminomethanesulphinic acid
(5-carboxypentylamino)iminomethanesulphinic acid
(hydroxymethylamino)iminomethanesulphinic acid
(2-aminoethylamino)iminomethanesulphinic acid
imino (sulphonylmethylamino) methanesulphinic acid
imino(2-sulphonylpropylamino)methane-sulphinic acid
imino(2-phosphonylmethylamino)methane-sulphinic acid
imino(phenylamino)methanesulphinic acid
imino(4-methylphenylamino)methanesulphinic acid
imino(4-hydroxyphenylamino)methanesulphinic acid
imino(4-methoxyphenylamino)methanesulphinic acid
imino(2-chlorophenylamino)methanesulphinic acid
imino(4-methyl-2-pyridylamino)methane-sulphinic acid
imino(6-methyl-2-pyridylamino)methane-sulphinic acid
imino(5-methyl-2-pyridylamino)methane-sulphinic acid
imino(2-quinolylamino)methanesulphinic acid
imino(3-quinolylamino)methanesulphinic acid
(methylimino)-2-pyridylaminomethane-sulphinic acid
(methylimino) [(3,4,5,6-tetrahydro-2-pyridyl)amino]methanesulphinic acid
[(aminoiminomethyl)amino]iminomethane-sulphinic acid.

Preference is very particularly given to:
(carboxymethylamino)iminomethanesulphinic acid, and
imino(phenylamino)methanesulphinic acid.

Mention may also be made, among the derivatives corresponding to the general formula (I) which are particularly well suited to the reducing compositions according to the invention, of those disclosed in Patent JP 93 239662, filed by Fuji.

The formamidinesulphinic acid derivative of formula (I) is advantageously formulated as an aqueous lotion, at a pH of between 2 and 11 and preferably between 7 and 10.

In accordance with the invention, the name "formamidinesulphinic acid" is equivalent to "amino-iminomethanesulphinic acid" or "thiourea dioxide".

The process in accordance with the invention for the permanent deformation of the hair comprises the application of a reducing composition comprising, as reducing agent, a compound of formula (I). The hair is shaped by using mechanical means well known to a person skilled in the art, such as curlers, the reducing composition being applied before and after the means for shaping the hair and a setting composition being applied after the reducing composition, with or without an intermediate or subsequent stage of rinsing or of application of intermediate composition.

According to the present invention, the permanent deformation of the hair preferably consists, in a first stage, in reducing the disulphide bonds of the keratin by application, for approximately 5 to 60 min, of a reducing composition as defined above and then, in a second stage, in reforming the said bonds by application of an oxidizing composition or optionally by allowing atmospheric oxygen to act.

Preferably, a reducing composition as defined above is applied to wet hair wound beforehand onto rollers having a diameter of 4 to 20 mm, it being possible for the composition optionally to be applied as the hair is wound on; the reducing composition is subsequently allowed to act for a time of 5 to 60 minutes, preferably of 5 to 30 minutes, and then the hair is copiously rinsed; after which an oxidizing composition which makes it possible to reform the disulphide bonds of the keratin is applied to the wound hair for a exposure time of 2 to 10 minutes. After having removed the rollers, the hair is copiously rinsed.

The oxidizing composition is of the type commonly used and comprises, for example, as oxidizing agent, hydrogen peroxide, an alkaline bromate, a persalt, a polythionate or a mixture of alkaline bromate and of persalt. The concentration of hydrogen peroxide can vary from 1 to 20 volumes and preferably from 1 to 10, the concentration of alkaline bromate from 2 to 12% and that of persalt from 1 to 15% by weight with respect to the total weight of the oxidizing composition. The pH of the oxidizing composition is generally between 2 and 10. This oxidation can be carried out immediately or can be delayed.

The deformation of the hair according to the invention can also consist of a process for straightening the hair, in which a reducing composition according to the invention is applied to the hair and then the hair is subjected to a mechanical deformation which makes it possible to set it in its new form by an operation in which the hair is smoothed with a wide-toothed comb, with the back of a comb or with the hand. After an exposure time of 5 to 60 minutes, in particular of 5 to 30 minutes, a fresh smoothing is then carried out, then the hair is carefully rinsed and an oxidizing or setting composition as defined above is applied, which composition is allowed to act for approximately 2 to 10 minutes, and then the hair is copiously rinsed.

In the perming compositions according to the invention, the reducing agent of general formula (I) is generally present at a concentration of between 0.05 and 20% and preferably between 0.1 and 8% by weight with respect to the total weight of the reducing composition.

The pH of the composition is preferably between 4 and 11 and more particularly between 6 and 10 and is obtained using an alkaline agent, such as, for example, aqueous ammonia, monoethanolamine, diethanolamine, triethanolamine, 1,3-propanediamine, an alkali metal or ammonium carbonate or bicarbonate, an organic carbonate, such as guanidine carbonate, or an alkaline hydroxide, or using an acidifying agent, such as, for example, hydrochloric acid, acetic acid, lactic acid, oxalic acid or boric acid.

The reducing composition can also comprise, in combination, another known reducing agent, such as, for example, thioglycolic acid, glyceryl or glycol monothioglycolate, cysteamine and its C1–C4 acylated derivatives, such as N-acetylcysteamine or N-propionyl-cysteamine, cysteine, N-acetylcysteine, the N-mercapto-alkylamides of sugars, such as N-(2-mercaptoethyl)-gluconamide, β-mercaptopropionic acid and its derivatives, thiolactic acid and its esters, such as glyceryl monothiolactate, thiomalic acid, pantheteine, thioglycerol, sulphites or bisulphites of an alkali metal or alkaline earth metal, the N-(mercaptoalkyl)-o-hydroxyalkylamides disclosed in Patent Application EP 354 835 and the N-mono- or N,N-dialkylmercapto-4-butyramides disclosed in Patent Application EP 368 763, the aminomercaptoalkylamides disclosed in Patent Application EP 403 267 and the alkylamino-mercaptoalkylamides disclosed in Patent Application EP 432 000.

According to a preferred embodiment, the reducing composition also comprises a surface-active agent of nonionic, anionic, cationic or amphoteric type and mention may be made, among these, of alkyl sulphates, alkylbenzenesulphates, alkyl ether sulphates, alkylsulphonates, quaternary ammonium salts, alkyl betaines, oxyethylenated alkylphenols, fatty acid alkanolamides, oxyethylenated fatty acid esters and other nonionic surfactants of the hydroxypropyl ether type.

When the reducing composition comprises at least one surface-active agent, the latter is generally present at a maximum concentration of 30% by weight and preferably of between 0.5 and 10% by weight with respect to the total weight of the reducing composition.

With the aim of improving the cosmetic properties of the hair or alternatively of lessening or preventing their damage to them, the reducing composition can also comprise a treating agent of cationic, anionic, nonionic or amphoteric nature.

Mention may in particular be made, among the particularly preferred treating agents, of those disclosed in French Patents No. 2 598 613 and No. 2 470 596. Use may also be made, as treating agents, of volatile or nonvolatile and linear or cyclic silicones and their mixtures, polydimethylsiloxanes, quaternized polyorganosiloxanes, such as those disclosed in French Patent Application No. 2 535 730, polyorganosiloxanes with aminoalkyl groups modified by alkoxycarbonylalkyl groups, such as those disclosed in U.S. Pat. No. 4,749,732, polyorganosiloxanes, such as the polydimethylsiloxane-polyoxyalkyl copolymer of the dimethicone copolyol type, a polydimethylsiloxane with stearoxy end groups (stearoxy dimethicone), a polydimethylsiloxane-dialkylammonium acetate copolymer or a polydimethylsiloxane-poly(alkyl betaine) copolymer which are disclosed in British Patent No. 2 197 352, polysiloxanes organomodified by mercapto or mercapto-alkyl groups such as those disclosed in French Patent No. 1 530 369 and in European Patent Application No. 295 780, and silanes, such as stearoxytrimethylsilane.

The reducing composition can also comprise other treating ingredients, such as cationic polymers, such as those used in the compositions of French Patents Nos. 79.32078 (2 472 382) and 80.26421 (2 495 931), or cationic polymers of the ionene type, such as those used in the compositions of Luxembourgian Patent No. 83 703, basic amino acids (such as lysine or arginine) or acidic amino acids (such as glutamic acid or aspartic acid), peptides and their derivatives, protein hydrolysates, waxes, swelling and penetrating agents or agents which make it possible to reinforce the effectiveness of the reducing agent, such as the SiO2/PDMS (polydimethylsiloxane) mixture, dimethyliso-sorbitol, urea and its derivatives, pyrrolidone, N-alkylpyrrolidones, thiamorpholinone, or alkyl ethers of alkylene glycol or of dialkylene glycol, such as, for example, propylene glycol monomethyl ether, dipropylene glycol monomethyl ether, ethylene glycol monoethyl ether and diethylene glycol monoethyl ether, C3–C6 alkanediols, such as, for example, 1,2-propane-diol and 1,2-butanediol, 2-imidazolidinone and other compounds, such as fatty alcohols, lanolin derivatives, active ingredients, such as panthothenic acid, agents for combating hair loss, antidandruff agents, thickeners, suspending agents, sequestering agents, opacifying agents, colorants or sunscreen agents, as well as fragrances and preservatives.

The reducing composition according to the invention is provided essentially in the aqueous form, in particular in the form of a thickened or non-thickened lotion, of a cream or of a gel.

The reducing composition according to the invention can also be of the exothermic type, that is to say of the type which gives rise to a degree of warming when applied to the hair, which is pleasing to the person who is undergoing the first stage of the perming or hair straightening.

The reducing composition according to the invention can also comprise a solvent, such as, for example, ethanol, propanol or isopropanol, or glycerol, at a maximum concentration of 20% with respect to the total weight of the composition.

The vehicle of the compositions according to the invention is preferably water or an aqueous/alcoholic solution of a lower alcohol, such as ethanol, isopropanol or butanol.

When the compositions are intended for an operation for straightening the hair, the reducing composition is preferably in the form of a thickened cream, so as to keep the hair as straight as possible. These creams are prepared in the form of "heavy" emulsions, for example based on glyceryl stearate, on glycol stearate, on self-emulsifiable waxes or fatty alcohols.

It is also possible to use liquids or gels comprising thickening agents, such as carboxyvinyl polymers or copolymers which "stick" the hair together and keep it in the smooth position during the exposure time.

The invention also relates to a kit, in particular for the permanent deformation of the hair, comprising, in a first compartment, as reducing composition, a composition according to the invention comprising a compound of formula (I) and, in a second compartment, an oxidizing composition.

The invention may be better understood with the help of the following nonlimiting example which constitutes a preferred embodiment of the compositions according to the invention.

EXAMPLES

A lotion 1 in accordance with the prior art, comprising formamidinesulphinic acid as reducing agent, and a lotion 2 in accordance with the present invention, comprising a derivative of formula I, namely N-phenylformamidinesulphinic acid, as reducing agent, are prepared. The compositions of these two lotions are shown in Table I below.

TABLE I

|  | Lotion 1 | Lotion 2 |
| --- | --- | --- |
| Formamidinesulphinic acid | 0.5 M | — |
| N-Phenylformamidine-sulphinic acid | — | 0.5 M |
| Diethylenetriamine-pentaacetic acid, pentasodium salt, as an aqueous solution comprising 40% a.m. | 0.2 g | 0.2 g |
| Monoethanolamine | q.s. for pH 9 | q.s. for pH 9 |
| Water | q.s. for 100 g | q.s. for 100 g |

The lotion 1 or 2 is applied to locks of natural European chestnut-brown hair. Curls are formed using curlers. The lotion is allowed to act on the wound hair for 15 minutes. The combination is dried with a hairdryer for 5 minutes. The hair is rinsed with water. A conventional setting composition based on hydrogen peroxide is applied. Rinsing is again carried out. The curlers are removed.

It is observed that, with the lotion 1 in accordance with the prior art, the modification in the shape of the hair is slight, whereas the lotion 2 produces a much greater and more marked deformation in the shape of the hair.

The invention claimed is:

1. A reducing composition for permanent deformation of hair comprising at least one reducing agent chosen from N-substituted formamidinesulphinic acid derivatives of formula (I), the inorganic salts thereof, and the organic salts thereof:

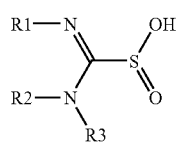

in which:
R1, R2, and R3, which are identical or different, are each chosen from hydrogen; amino groups; $C_1$ to $C_8$ aminoiminoalkyl groups; imino groups; $C_1$ to $C_8$ aminoalkyl groups; guanidino groups; $C_1$ to $C_8$ linear alkyl groups; $C_1$ to $C_8$ branched alkyl groups; $C_2$ to $C_8$ linear alkenyl groups; $C_2$ to $C_8$ branched alkenyl groups; $C_7$ to $C_{20}$ aralkyl groups; and phenyl groups optionally substituted by at least one group chosen from halogens, $C_1$ to $C_4$ alkyl groups, $C_1$ to $C_4$ alkoxy groups, and hydroxyl groups; and
wherein said R1, R2, and R3 are optionally substituted; with the proviso that when R1 is hydrogen or $C_1$ to $C_4$ alkyl, then R2 and R3 are not simultaneously hydrogen, or hydrogen and $C_1$ to $C_4$ alkyl,
the composition further comprising at least one additive chosen from reducing agents other than said at least one reducing agent; surface-active agents chosen from nonionic surface-active agents, anionic surface-active agents, cationic surface-active agents, and amphoteric surface-active agents; treating agents chosen from cationic treating agents, anionic treating agents, nonionic treating agents, and amphoteric treating agents; fatty alcohols; lanolin derivatives; active ingredients; agents for combating hair loss; antidandruff agents; thickeners; suspending agents; sequestering agents; opacifying agents; colorants; sunscreen agents; fragrances; and preservatives.

2. A composition according to claim 1, wherein said R1, R2, and R3, which are identical or different, are each chosen from hydrogen; linear $C_1$ to $C_6$ alkyl groups optionally substituted by at least one group chosen from hydroxyl groups, carboxyl groups, amino groups, sulphonyl groups, and phosphonyl groups; branched $C_1$ to $C_6$ alkyl groups optionally substituted by at least one group chosen from hydroxyl groups, carboxyl groups, amino groups, sulphonyl groups, and phosphonyl groups; phenyl groups optionally substituted by at least one group chosen from halogens, $C_1$ to $C_4$ alkyl groups, $C_1$ to $C_4$ alkoxy groups, and hydroxyl groups; and guanidino groups.

3. A composition according to claim 1, wherein said at least one reducing agent is chosen from:
(dimethylamino)iminomethanesulphinic acid;
(diethylamino)iminomethanesulphinic acid;
(phenylamino)(phenylimino)methanesulphinic acid;
(phenylmethylamino)(phenylmethylimino)methanesulphinic acid;
(carboxymethylamino)iminomethanesulphinic acid;
(2-carboxyethylamino)iminomethanesulphinic acid;
(3-carboxypropylamino)iminomethanesulphinic acid;
(5-carboxypentylamino)iminomethanesulphinic acid;
(hydroxymethylamino)iminomethanesulphinic acid;
(2-aminoethylamino)iminomethanesulphinic acid;
imino(sulphonylmethylamino)methanesulphinic acid;
imino(2-sulphonylpropylamino)methanesulphinic acid;
imino(2-phosphonylmethylamino)methanesulphinic acid;
imino(phenylamino)methanesulphinic acid;
imino(4-methylphenylamino)methanesulphinic acid;
imino(4-hydroxyphenylamino)methanesulphinic acid;
imino(4-methoxyphenylamino)methanesulphinic acid;
imino(2-chlorophenylamino)methanesulphinic acid;
[(aminoiminomethyl)amino]iminomethanesulphinic acid.

4. A composition according to claim 1, wherein said at least one reducing agent is chosen from:
(carboxymethylamino)iminomethanesulphinic acid; and
imino(phenylamino)methanesulphinic acid.

5. A composition according to claim 1, wherein said at least one reducing agent is present in an amount ranging from 0.05% to 20% by weight with respect to the total weight of said composition.

6. A composition according to claim 1, wherein said at least one reducing agent is present in an amount ranging from 0.1% to 8% by weight with respect to the total weight of said composition.

7. A composition according to claim 1, wherein said composition has a pH ranging from 2 to 11.

8. A composition according to claim 1, wherein said composition has a pH ranging from 7 to 10.

9. A composition according to claim 1, wherein said reducing agents other than said at least one reducing agent are chosen from thioglycolic acid; glyceryl monothioglycolate; glycol monothioglycolate; cysteamine; $C_1$ to $C_4$ acylated derivatives of cysteamine; cysteine; N-acetylcysteine; N-mercaptoalkylamides of sugars; β-mercaptopropionic acid; derivatives of β-mercaptopropionic acid; thiolactic acid; thioloactic esters; thiomalic acid; pantheteine; thioglycerol; sulphites of at least one alkali metal; sulphites of at least one alkaline earth metal; bisulphites of at least one alkali metal; bisulphites of at least one alkaline earth metal; N-(mercaptoalkyl)-o-hydroxyalkylamides; N-monoalkylmercapto-4-butyramides; N,N-dialkylmercapto-4-butyramides; aminomercaptoalkylamides; and alkylaminomercaptoalkylamides.

10. A composition according to claim 9, wherein said derivatives of cysteamine are chosen from N-acetylcysteamine and N-propionylcysteamine.

11. A composition according to claim 9, wherein said N-mercaptoalkylamides of sugars are chosen from N-(2-mercaptoethyl)-gluconamide.

12. A composition according to claim 9, wherein said thioloactic esters are chosen from glyceryl monothiolactate.

13. A composition according to claim 1, wherein said surface-active agents are chosen from alkyl sulphates; alkylbenzenesulphates; alkyl ether sulphates; alkylsulphonates; quaternary ammonium salts; alkyl betaines; oxyethylenated alkylphenols; fatty acid alkanolamides; oxyethylenated fatty acid esters; and nonionic surfactants comprising at least one hydroxypropyl ether group.

14. A composition according to claim 1, wherein said treating agents are chosen from volatile linear silicones; volatile cyclic silicones; nonvolatile linear silicones; nonvolatile cyclic silicones; polydimethylsiloxanes; quaternized polyorganosiloxanes; polyorganosiloxanes with at least one aminoalkyl group modified by at least one alkoxy-carbonylalkyl group; polyorganosiloxanes; polydimethylsiloxanes with stearoxy end groups (stearoxy dimethicone); polydimethylsiloxane-dialkylammonium acetate copolymers; poly-dimethylsiloxane-poly(alkyl betaine) copolymers; polysiloxanes organomodified by at least one group chosen from mercapto groups and mercaptoalkyl groups; silanes; cationic polymers; basic amino acids; acidic amino acids; peptides; derivatives of peptides; protein hydrolysates; waxes; swelling agents; penetrating agents; agents which make it possible to reinforce the effectiveness of said at least one reducing agent; dimethylisosorbitol; urea; derivatives of urea; pyrrolidone; N-alkylpyrrolidones; thiamorpholinone; alkyl ethers of alkylene glycol; alkyl ethers of dialkylene glycol; $C_3$ to $C_6$ alkanediols; and 2-imidazolidinone.

15. A composition according to claim 14, wherein said polyorganosiloxanes are chosen from polydimethylsiloxane-polyoxyalkyl copolymers.

16. A composition according to claim 14, wherein said silanes are chosen from stearoxytrimethylsilane.

17. A composition according to claim 14, wherein said cationic polymers are chosen from cationic polymers derived from ionene.

18. A composition according to claim 14, wherein said basic amino acids are chosen from lysine and arginine.

19. A composition according to claim 14, wherein said acidic amino acids are chosen from glutamic acid and aspartic acid.

20. A composition according to claim 14, wherein said agents which make it possible to reinforce the effectiveness of said at least one reducing agent are chose from $SiO_2$/polydimethylsiloxane mixtures.

21. A composition according to claim 14, wherein said alkyl ethers of alkylene glycol are chosen from propylene glycol monomethyl ether, and ethylene glycol monoethyl ether.

22. A composition according to claim 14, wherein said alkyl ethers of dialkylene glycol are chosen from dipropylene glycol monomethyl ether and diethylene glycol monoethyl ether.

23. A composition according to claim 14, wherein said $C_3$ to $C_6$ alkanediols are chosen from 1,2-propanediol and 1,2-butanediol.

24. A composition according to claim 1, wherein said active ingredients are chosen from panthothenic acid.

25. A composition according to claim 1, wherein said composition is a lotion, optionally thickened, a cream, or a gel.

26. A composition according to claim 1, wherein said composition is an exothermic composition.

27. A composition according to claim 1, further comprising water.

28. A composition according to claim 1, further comprising at least one solvent.

29. A composition according to claim 28, wherein said at least one solvent is chosen from ethanol, propanol, butanol, isopropanol, and glycerol.

30. A composition according to claim 28, wherein said at least one solvent is present in an amount ranging up to 20% by weight with respect to the total weight of said composition.

31. A reducing composition for permanent deformation of hair comprising at least one reducing agent chosen from N-substituted formamidinesulphinic acid derivatives of formula (I), the inorganic salts thereof, and the organic salts thereof:

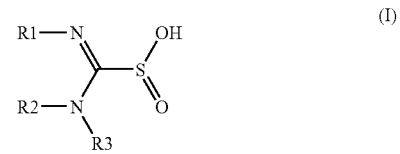

wherein:
R1, R2 and R3, which are identical or different, are each chosen from hydrogen; amino groups; $C_1$ to $C_8$ aminoiminoalkyl groups; imino groups; $C_1$ to $C_8$ aminoalkyl groups; guanidino groups; $C_1$ to $C_8$ linear alkyl groups; $C_1$ to $C_8$ branched alkyl groups; $C_2$ to $C_8$ linear alkenyl groups; $C_2$ to $C_8$ branched alkenyl groups; $C_7$ to $C_{20}$ aralkyl groups; and phenyl groups optionally substituted by at least one group chosen from halogens, $C_1$ to $C_4$ alkyl groups, $C_1$ to $C_4$ alkoxy groups, and hydroxyl groups;

wherein R1, R2 and R3 are each optionally substituted with at least one substituent chosen from hydroxyl groups; carboxyl groups; amino groups; amido groups; halogens; $C_1$ to $C_8$ linear alkyl groups; $C_1$ to $C_8$ branched alkyl groups; $C_1$ to $C_8$ linear alkoxy groups; $C_1$ to $C_8$ branched alkoxy groups; sulphonyl groups; sulphonate groups; phosphonyl groups; phosphate groups; $C_1$ to $C_8$ linear alkyl groups substituted with at least one group chosen from sulphonic acid groups, sulphonate groups, phosphoric acid groups, phosphate groups, amino groups, and $C_1$ to $C_8$ alkoxy groups; $C_1$ to $C_8$ branched alkyl groups substituted with at least one group chosen from sulphonic acid groups, sulphonate groups, phosphoric acid groups, phosphate groups, amino groups, and $C_1$ to $C_8$ alkoxy groups; $C_2$ to $C_8$ linear alkenyl groups substituted with at least one group chosen from sulphonic acid groups, sulphonate groups, phosphoric acid groups, phosphate groups, amino groups, and $C_1$ to $C_8$ alkoxy groups; $C_2$ to $C_8$ branched alkenyl groups substituted with at least one group chosen from sulphonic acid groups, sulphonate groups, phosphoric acid groups, phosphate groups, amino groups, and $C_1$ to $C_8$ alkoxy groups; and $C_7$ to $C_{20}$ aralkyl groups substituted with at least one group chosen from sulphonic acid groups, sulphonate groups, phosphoric acid groups, phosphate groups, amino groups, and $C_1$ to $C_8$ alkoxy groups;

with the Proviso that when R1 is hydrogen or $C_1$ to $C_4$ alkyl, then R2 and R3 are not simultaneously hydrogen, or hydrogen and $C_1$ to $C_4$ alkyl, the composition further comprising at least one additive chosen from reducing agents other than said at least one reducing agent; surface-active agents chosen from nonionic surface-active agents, anionic surface-active agents, cationic surface-active agents, and amphoteric surface-active agents; treating agents chosen from cationic treating agents, anionic treating agents, nonionic treating agents, and amphoteric treating agents; fatty alcohols; lanolin derivatives; active ingredients; agents for combating hair loss; antidandruff agents; thickeners; suspending agents; sequestering agents; opacifying agents; colorants; sunscreen agents; fragrances; and preservatives.

32. A reducing composition for permanent deformation of hair comprising at least one reducing agent chosen from N-substituted formamidinesulphinic acid derivatives of formula (I), the inorganic salts thereof, and the organic salts thereof:

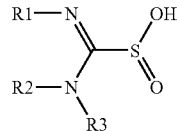

wherein:
(a) R1, R2 and R3, which are identical or different, are each chosen from hydrogen; amino groups; $C_1$ to $C_8$ aminoiminoalkyl groups; imino groups; $C_1$ to $C_8$ aminoalkyl groups; guanidino groups; $C_1$ to $C_8$ linear alkyl groups; $C_1$ to $C_8$ branched alkyl groups; $C_2$ to $C_8$ linear alkenyl groups; $C_2$ to $C_8$ branched alkenyl groups; $C_7$ to $C_{20}$ aralkyl groups; and phenyl groups optionally substituted by at least one group chosen from halogens, $C_1$ to $C_4$ alkyl groups, $C_1$ to $C_4$ alkoxy groups, and hydroxyl groups;
wherein R1, R2 and R3 are each optionally substituted with at least one substituent chosen from hydroxyl groups, carboxyl groups, amino groups, amido groups, halogen groups, $C_1$ to $C_8$ linear alkyl groups, $C_1$ to $C_8$ branched alkyl groups, C, to $C_8$ linear alkoxy groups, and $C_1$ to $C_8$ branched alkoxy groups; and
(b) at least one of R1, R2, and R3 is chosen from amino groups; $C_1$ to $C_8$ aminoalkyl groups; $C_1$ to $C_8$ linear alkyl groups; $C_1$ to $C_8$ branched alkyl groups; $C_2$ to $C_8$ linear alkenyl groups; $C_2$ to $C_8$ branched alkenyl groups; $C_7$ to $C_{20}$ aralkyl groups; and phenyl groups optionally substituted by at least one group chosen from halogens, $C_1$ to $C_4$ alkyl groups, $C_1$ to $C_4$ alkoxy groups, and hydroxyl groups;
wherein said at least one of R1, R2 and R3 is optionally substituted with at least one group chosen from sulphonyl groups; sulphonate groups; phosphonyl groups; phosphate groups; amino groups; $C_1$ to $C_8$ linear alkoxy groups; $C_1$ to $C_8$ branched alkoxy groups; $C_1$ to $C_8$ linear alkyl groups substituted with at least one group chosen from sulphonic acid groups, sulphonate groups, phosphoric acid groups, phosphate groups, amino groups, $C_1$ to $C_8$ linear alkoxy groups, and $C_1$ to $C_8$ branched alkoxy groups; $C_1$ to $C_8$ branched alkyl groups substituted with at least one group chosen from sulphonic acid groups, sulphonate groups, phosphoric acid groups, phosphate groups, amino groups, $C_1$ to $C_8$ linear alkoxy groups, and $C_1$ to $C_8$ branched alkoxy groups; $C_2$ to $C_8$ linear alkenyl groups substituted with at least one group chosen from sulphonic acid groups, sulphonate groups, phosphoric acid groups, phosphate groups, amino groups, $C_1$ to $C_8$ linear alkoxy groups, and $C_1$ to $C_8$ branched alkoxy groups; $C_2$ to $C_8$ branched alkenyl groups substituted with at least one group chosen from sulphonic acid groups, sulphonate groups, phosphoric acid groups, phosphate groups, amino groups, $C_1$ to $C_8$ linear alkoxy groups, and $C_1$ to C8 branched alkoxy groups; and $C_7$ to $C_{20}$ aralkyl groups substituted with at least one group chosen from sulphonic acid groups, sulphonate groups, phosphoric acid groups, phosphate groups, amino groups, $C_1$ to $C_8$ linear alkoxy groups, and $C_1$ to $C_8$ branched alkoxy groups;

with the proviso that when R1 is hydrogen or $C_1$ to $C_4$ alkyl, then R2 and R3 are not simultaneously hydrogen, or hydrogen and $C_1$ to $C_4$ alkyl,
the composition further comprising at least one additive chosen from reducing agents other than said at least one reducing agent; surface-active agents chosen from nonionic surface-active agents, anionic surface-active agents, cationic surface-active agents, and amphoteric surface-active agents; treating agents chosen from cationic treating agents, anionic treating agents, nonionic treating agents, and amphoteric treating agents; fatty alcohols; lanolin derivatives; active ingredients; agents for combating hair loss; antidandruff agents; thickeners; suspending agents; sequestering agents; opacifying agents; colorants; sunscreen agents; fragrances; and preservatives.

33. A process for permanent deformation of hair comprising applying at least one reducing composition comprising at least one reducing agent chosen from N-substituted formamidinesulphinic acid derivatives of formula (I), the inorganic salts thereof, and the organic salts thereof:

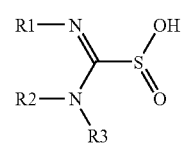

wherein:
R1, R2, and R3, which are identical or different, are each chosen from hydrogen;
amino groups; $C_1$ to $C_8$ aminoiminoalkyl groups; imino groups; $C_1$ to $C_8$ aminoalkyl groups; guanidino groups; $C_1$ to $C_8$ linear alkyl groups; $C_1$ to $C_8$ branched alkyl groups; $C_2$ to $C_8$ linear alkenyl groups; $C_2$ to C8 branched alkenyl groups; $C_7$ to $C_{20}$ aralkyl groups; and phenyl groups optionally substituted by at least one group chosen from halogens, $C_1$ to $C_4$ alkyl groups, $C_1$ to $C_4$ alkoxy groups, and hydroxyl groups; and
wherein said R1, R2, and R3 are optionally substituted;
with the proviso that when R1 is hydrogen or $C_1$ to $C_4$ alkyl, then R2 and R3 are not simultaneously hydrogen, or hydrogen and $C_1$ to $C_4$ alkyl,
the composition further comprising at least one additive chosen from reducing agents other than said at least one reducing agent: surface-active agents chosen from nonionic surface-active agents, anionic surface-active agents, cationic surface-active agents, and amphoteric surface-active agents; treating agents chosen from cationic treating agents, anionic treating agents, nonionic treating agents, and amphoteric treating agents; fatty alcohols; lanolin derivatives; active ingredients; agents for combating hair loss; antidandruff agents; thickeners; suspending agents; sequestering agents; opacifying agents; colorants; sunscreen agents; fragrances; and preservatives.

34. A process according to claim 33, further comprising shaping said hair.

35. A process according to claim 34, wherein said at least one reducing composition is applied before or after said shaping.

36. A process according to claim 34, wherein said at least one reducing composition is applied before and after said shaping.

37. A process according to claim 33, further comprising applying at least one setting composition.

38. A process according to claim 37, where said at least one setting composition is applied after application of said at least one reducing composition.

39. A process according to claim 33, further comprising rinsing said at least one reducing composition from said hair.

40. A process according to claim 33, further comprising rinsing said at least one setting composition from said hair.

41. A process according to claim 39, further comprising applying at least one composition other than said at least one reducing composition and said at least one setting composition.

42. A process according to claim 33, wherein said at least one reducing composition is applied to said hair for a sufficient period of time to reduce at least one disulphide bond of the keratin of said hair.

43. A process according to claim 33, wherein said sufficient period of time to reduce at least one disulphide bond of the keratin of said hair ranges from 5 minutes to 60 minutes.

44. A process according to claim 43, wherein said sufficient period of time to reduce at least one disulphide bond of the keratin of said hair ranges from 5 minutes to 30 minutes.

45. A process according to claim 41, further comprising applying at least one oxidizing composition to said hair.

46. A process according to claim 45, wherein said at least one oxidizing composition is applied to said hair after the application of said at least one reducing composition to said hair.

47. A process according to claim 46, wherein said at least one oxidizing composition is applied to said hair after said at least one reducing composition is rinsed from said hair.

48. A process according to claim 45, wherein said at least one oxidizing composition is applied to said hair for a sufficient period of time to reform at least one disulphide bond of the keratin of said hair.

49. A process according to claim 48, wherein said sufficient period of time to reform at least one disulphide bond of the keratin of said hair ranges from 2 minutes to 10 minutes.

50. A process according to claim 48, further comprising rinsing said hair after said a sufficient period of time to reform at least one disulphide bond of the keratin of said hair.

51. A process according to claim 45, wherein said at least one oxidizing composition comprises at least one oxidizing agent.

52. A process according to claim 51, wherein said at least one oxidizing agent is chosen from hydrogen peroxide; alkaline bromates; persalts; and polythionates.

53. A process according to claim 45, wherein said at least one oxidizing composition has a pH ranging from 2 to 10.

54. A process according to claim 33, wherein said R1, R2, and R3, which are identical or different, are each chosen from hydrogen; linear $C_1$ to $C_6$ alkyl groups optionally substituted by at least one group chosen from hydroxyl groups, carboxyl groups, amino groups, sulphonyl groups, and phosphonyl groups; branched $C_1$ to $C_6$ alkyl groups optionally substituted by at least one group chosen from hydroxyl groups, carboxyl groups, amino groups, sulphonyl groups, and phosphonyl groups; phenyl groups optionally substituted by at least one group chosen from halogens, $C_1$ to $C_4$ alkyl groups, $C_1$ to $C_4$ alkoxy groups, and hydroxyl groups; and guanidino groups.

55. A process according to claim 33, wherein said at least one reducing agent is chosen from:
imino(methylamino)methanesulphinic acid;
imino(propylamino)methanesulphinic acid;
(dimethylamino)iminomethanesulphinic acid;
(diethylamino)iminomethanesulphinic acid;
(ethylamino)(ethylimino)methanesulphinic acid;
(methylamino)(methylimino)methanesulphinic acid;
(ethylamino)(ethylimino)methanesulphinic acid;
(butylamino)(butylimino)methanesulphinic acid;
(phenylamino)(phenylimino)methanesulphinic acid;
(phenylmethylamino)(phenylmethylimino) methanesulphinic acid;
(carboxymethylamino)iminomethanesulphinic acid;
(2-carboxyethylamino)iminomethane sulphinic acid;
(3-carboxypropylamino)iminomethane sulphinic acid;
(5-carboxypentylamino)iminomethane sulphinic acid;
(hydroxymethylamino)iminomethanesulphinic acid;
(2-aminoethylamino)iminomethanesulphinic acid;
imino(sulphonylmethylamino)methanesulphinic acid;
imino(2-sulphonylpropylamino)methane sulphinic acid;
imino(2-phosphonylmethylamino)methane sulphinic acid;
imino(phenylamino)methanesulphinic acid;
imino(4-methylphenylamino)methanesulphinic acid;
imino(4-hydroxyphenylamino)methanesulphinic acid;
imino(4-methoxyphenylamino)methanesulphinic acid;
imino(2-chlorophenylamino)methanesulphinic acid;
[(aminoiminomethyl)amino]iminomethane sulphinic acid.

56. A process according to claim 33, wherein said at least one reducing agent is chosen from:
(carboxymethylamino)iminomethanesulphinic acid; and
imino(phenylamino)methanesulphinic acid.

57. A process according to claim 33, wherein said at least one reducing agent is present in said at least one reducing composition in an amount ranging from 0.05% to 20% by weight with respect to the total weight of said composition.

58. A process according to claim 33, wherein said at least one reducing agent is present in said at least one reducing composition in an amount ranging from 0.1% to 8% by weight with respect to the total weight of said composition.

59. A process according to claim 33, wherein said at least one reducing composition has a pH ranging from 2 to 11.

60. A process according to claim 33, wherein said at least one reducing composition has a pH ranging from 7 to 10.

61. A process according to claim 33, wherein said reducing agents other than said at least one reducing agent are chosen from thioglycolic acid; glyceryl monothioglycolate; glycol monothioglycolate; cysteamine; $C_1$ to $C_4$ acylated derivatives of cysteamine; cysteine; N-acetylcysteine; N-mercaptoalkylamides of sugars; β-mercaptopropionic acid; derivatives of β-mercaptopropionic acid; thiolactic acid; thioloactic esters; thiomalic acid; pantheteine; thioglycerol; sulphites of at least one alkali metal; sulphites of at least one alkaline earth metal; bisulphites of at least one alkali metal; bisulphites of at least one alkaline earth metal; N-(mercaptoalkyl)-o-hydroxyalkylamides; N-monoalkylmercapto-4-butyramides; N,N-dialkylmercapto-4-butyramides; aminomercaptoalkylamides; and alkylaminomercaptoalkylamides.

62. A process according to claim 33, wherein said derivatives of cysteamine are chosen from N-acetylcysteamine and N-propionylcysteamine.

63. A process according to claim 33, wherein said N-mercaptoalkylamides of sugars are chosen from N-(2-mercaptoethyl)-gluconamide.

64. A process according to claim 61, wherein said thioloactic esters are chosen from glyceryl monothiolactate.

65. A process according to claim 33, wherein said surface-active agents are chosen from alkyl sulphates; alkylbenzenesulphates; alkyl ether sulphates; alkylsulphonates; quaternary ammonium salts; alkyl betaines; oxyethylenated alkylphenols; fatty acid alkanolamides; oxyethylenated fatty acid esters; and nonionic surfactants comprising at least one hydroxypropyl ether group.

66. A process according to claim 33, wherein said treating agents are chosen from volatile linear silicones; volatile cyclic silicones; nonvolatile linear silicones; nonvolatile cyclic silicones; polydimethylsiloxanes; quaternized polyorganosiloxanes; polyorganosiloxanes with at least one aminoalkyl group modified by at least one alkoxy-carbonylalkyl group; polyorganosiloxanes; polydimethylsiloxanes with stearoxy end groups (stearoxy dimethicone); polydimethylsiloxane-dialkylammonium acetate copolymers; polydimethylsiloxane-poly(alkyl betaine) copolymers; polysiloxanes organomodified by at least one group chosen from mercapto groups and mercaptoalkyl groups; silanes; cationic polymers; basic amino acids; acidic amino acids; peptides; derivatives of peptides; protein hydrolysates; waxes; swelling agents; penetrating agents; agents which make it possible to reinforce the effectiveness of said at least one reducing agent; dimethylisosorbitol; urea; derivatives of urea; pyrrolidone; N-alkylpyrrolidones; thiamorpholinone; alkyl ethers of alkylene glycol; alkyl ethers of dialkylene glycol; $C_3$ to $C_6$ alkanediols; and 2-imidazolidinone.

67. A process according to claim 66, wherein said polyorganosiloxanes are chosen from polydimethylsiloxane-polyoxyalkyl copolymers.

68. A process according to claim 66, wherein said silanes are chosen from stearoxytrimethylsilane.

69. A process according to claim 66, wherein said cationic polymers are chosen from cationic polymers derived from ionene.

70. A process according to claim 66, wherein said basic amino acids are chosen from lysine and arginine.

71. A process according to claim 66, wherein said acidic amino acids are chosen from glutamic acid and aspartic acid.

72. A process according to claim 66, wherein said agents which make it possible to reinforce the effectiveness of said at least one reducing agent are chose from $SiO_2$/polydimethylsiloxane mixtures.

73. A process according to claim 66, wherein said alkyl ethers of alkylene glycol are chosen from propylene glycol monomethyl ether, and ethylene glycol monoethyl ether.

74. A process according to claim 66, wherein said alkyl ethers of dialkylene glycol are chosen from dipropylene glycol monomethyl ether and diethylene glycol monoethyl ether.

75. A process according to claim 66, wherein said $C_3$ to $C_6$ alkanediols are chosen from 1,2-propanediol and 1,2-butanediol.

76. A process according to claim 33, wherein said active ingredients are chosen from panthothenic acid.

77. A process according to claim 33, wherein said at least one reducing composition is a lotion, optionally thickened, a cream, or a gel.

78. A process according to claim 33, wherein said at least one reducing composition is an exothermic composition.

79. A process according to claim 33, wherein said at least one reducing composition further comprises water.

80. A process according to claim 33, wherein said at least one reducing composition comprises at least one solvent.

81. A process according to claim 80, wherein said at least one solvent is chosen from ethanol, propanol, butanol, isopropanol, and glycerol.

82. A process according to claim 80, wherein said at least one solvent is present in an amount ranging up to 20% by weight with respect to the total weight of said composition.

83. A process for permanent deformation of hair comprising applying at least one reducing composition comprising at least one reducing agent chosen from N-substituted formamidinesulphinic acid derivatives of formula (I), the inorganic salts thereof, and the organic salts thereof:

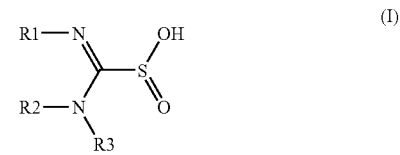

wherein:
R1, R2 and R3, which are identical or different, are each chosen from hydrogen; amino groups; $C_1$ to $C_8$ aminoiminoalkyl groups; imino groups; $C_1$ to $C_8$ aminoalkyl groups; guanidino groups; $C_1$ to $C_8$ linear alkyl groups; $C_1$ to $C_8$ branched alkyl groups; $C_2$ to $C_8$ linear alkenyl groups; $C_2$ to $C_8$ branched alkenyl groups; $C_7$ to $C_{20}$ aralkyl groups; and phenyl groups optionally substituted by at least one group chosen from halogens, $C_1$ to $C_4$ alkyl groups, $C_1$ to $C_4$ alkoxy groups, and hydroxyl groups;

wherein R1, R2 and R3 are each optionally substituted with at least one substituent chosen from hydroxyl groups; carboxyl groups; amino groups; amido groups; halogens; $C_1$ to $C_8$ linear alkyl groups; $C_1$ to $C_8$ branched alkyl groups; $C_1$ to $C_8$ linear alkoxy groups; $C_1$ to $C_8$ branched alkoxy groups; sulphonyl groups; sulphonate groups; phosphonyl groups; phosphate groups; $C_1$ to $C_8$ linear alkyl groups substituted with at least one group chosen from sulphonic acid groups, sulphonate groups, phosphoric acid groups, phosphate groups, amino groups, and $C_1$ to $C_8$ alkoxy groups; $C_1$ to $C_8$ branched alkyl groups substituted with at least one group chosen from sulphonic acid groups, sulphonate groups, phosphoric acid groups, phosphate groups, amino groups, and $C_1$ to $C_8$ alkoxy groups; $C_2$ to $C_8$ linear alkenyl groups substituted with at least one group chosen from sulphonic acid groups, sulphonate groups, phosphoric acid groups, phosphate groups, amino groups, and $C_1$ to $C_8$ alkoxy groups; $C_2$ to $C_8$ branched alkenyl groups substituted with at least one group chosen from sulphonic acid groups, sulphonate groups, phosphoric acid groups, phosphate groups, amino groups, and $C_1$ to $C_8$ alkoxy groups; and $C_7$ to $C_{20}$ aralkyl groups substituted with at least one group chosen from sulphonic acid groups, sulphonate groups, phosphoric acid groups, phosphate groups, amino groups, and $C_1$ to $C_8$ alkoxy groups;

with the proviso that when R1 is hydrogen or $C_1$ to $C_4$ alkyl then R2 and R3 are not simultaneously hydrogen, or hydrogen and $C_1$ to $C_4$ alkyl, the composition further comprising at least one additive chosen from reducing agents other than said at least one reducing agent; surface-active agents chosen from nonionic surface-active agents, anionic surface-active agents, cationic surface-active agents, and amphoteric surface-active agents: treating agents chosen from cationic treating agents, anionic treating agents, nonionic treating agents, and amphoteric treating agents; fatty alcohols; lanolin derivatives; active ingredients; agents for combating hair loss; antidandruff agents; thickeners; suspending agents; sequestering agents; opacifying agents; colorants: sunscreen agents; fragrances; and preservatives.

* * * * *

UNITED STATES PATENT AND TRADEMARK OFFICE
CERTIFICATE OF CORRECTION

| | | |
|---|---|---|
| PATENT NO. | : 7,070,770 B1 | Page 1 of 1 |
| APPLICATION NO. | : 09/714663 | |
| DATED | : July 4, 2006 | |
| INVENTOR(S) | : Nathalie Garnier et al. | |

It is certified that error appears in the above-identified patent and that said Letters Patent is hereby corrected as shown below:

On the title page, insert --Assignee: L'Oréal S.A., Paris (FR)--.

Claim 9, column 8,   line 37, "C$_1$to" should read --C$_1$ to--.
line 41, "thioloactic" should read --thiolactic--.

Claim 12, column 8,   line 56, "thioloactic" should read --thiolactic--.

Claim 20, column 9,   line 32, "chose" should read --chosen--.

Claim 31, column 10,   line 49, "Proviso" should read --proviso--.

Claim 32, column 11,   line 20, "optionallv" should read --optionally--.
line 28, "C," should read --C$_1$--.
line 62, "C8" should read --C$_8$--.

Claim 33, column 12,   line 38, "C8" should read --C$_8$--.
line 49, "agent:" should read --agent;--.

Claim 61, column 14,   line 54, "thioloactic" should read --thiolactic--.

Claim 64, column 15,   lines 1-2, "thioloactic" should read --thiolactic--.

Claim 72, column 15,   line 44, "chose" should read --chosen--.

Claim 83, column 17,   line 1, "agents:" should read --agents;--.

Claim 83, column 18,   line 2, "colorants:" should read --colorants;--.

Signed and Sealed this

Seventh Day of August, 2007

JON W. DUDAS
*Director of the United States Patent and Trademark Office*